United States Patent
Kraack et al.

(10) Patent No.: US 6,249,345 B1
(45) Date of Patent: Jun. 19, 2001

(54) CUVETTE

(75) Inventors: Jan Kraack, Hamburg; Kurt Harnack, Tangstedt; Wolfgang Goemann-Thoss, Hamburg; Rainer Treptow, Norderstedt, all of (DE)

(73) Assignee: Eppendorf-Netheler-Hinz GmbH, Hamburg (DE)

( * ) Notice: Subject to any disclaimer, the term of this patent is extended or adjusted under 35 U.S.C. 154(b) by 0 days.

(21) Appl. No.: 09/333,186

(22) Filed: Jun. 14, 1999

(30) Foreign Application Priority Data

Jun. 13, 1998 (DE) .............................. 198 26 470

(51) Int. Cl.$^7$ ..................................................... G01N 1/10
(52) U.S. Cl. ........................ 356/246; 356/244; 422/102; 422/104
(58) Field of Search .................................. 356/246, 244; 422/102, 104

(56) References Cited

U.S. PATENT DOCUMENTS

| | | |
|---|---|---|
| 3,506,367 | 4/1970 | Ross et al. . |
| 4,047,820 | 9/1977 | Sookak . |
| 4,207,289 | 6/1980 | Weiss . |
| 4,534,465 | 8/1985 | Rothermel at al. . |
| 5,116,578 | 5/1992 | Baxter . |
| 5,571,479 | * 11/1996 | Koch ..................................... 356/246 |
| 5,651,941 | 7/1997 | Stark et al. . |

FOREIGN PATENT DOCUMENTS

| | | |
|---|---|---|
| 0611028 | 5/1979 | (CH) . |
| 2252987 | 6/1973 | (DE) . |
| 2508527 | 5/1976 | (DE) . |
| 7638653 | 12/1976 | (DE) . |
| 2531136 | 2/1977 | (DE) . |
| 2609482 | 9/1977 | (DE) . |
| 2726498 | 12/1978 | (DE) . |
| 2810117 | 9/1979 | (DE) . |
| 2833187 | 2/1980 | (DE) . |
| 2922697 | 12/1980 | (DE) . |
| 3033618 | 4/1981 | (DE) . |
| 8533381 | 2/1986 | (DE) . |
| 8811948 | 11/1988 | (DE) . |
| 3832460 | 4/1989 | (DE) . |
| 1773333 | 7/1991 | (DE) . |
| 9502808 | 4/1995 | (DE) . |
| 2633004 | 7/1997 | (DE) . |
| 9472160 | 4/1998 | (DE) . |
| 0113118 | 7/1984 | (EP) . |
| 0365827 | 9/1989 | (EP) . |
| 0512368 | 11/1992 | (EP) . |
| 0668496 | 8/1995 | (EP) . |
| 9514235 | 5/1995 | (WO) . |

OTHER PUBLICATIONS

Cuvette for chemical analysis.
Patent abstract for Japanese Application No. 58–131540.
Catalogue of the firm "Hellma".

* cited by examiner

*Primary Examiner*—Frank G. Font
*Assistant Examiner*—Roy M. Punnoose
(74) *Attorney, Agent, or Firm*—Brown & Wood, LLP

(57) ABSTRACT

A cuvette for the measurement of the absorption of irradiation in liquid samples which at least in the regions of the windows is of a transparent plastic with an inner space which is formed in an essentially box-shaped upper part with an upper opening for filling and removing sample fluid and in an essentially box-shaped lower part which projects downwards from the floor of the upper part and which comprises a smaller cross section than the upper part, of maximally 200 $\mu l$ content capacity, two pairs of planar-parallel windows in the lower part which lie opposite one another, wherein the distance a of the one pair is different to the distance b of the windows of the other pair in order to make available differing layer thickness of the sample fluid for the measurement and with four feet which are flush with the four corners of the upper part and which extend away from the upper part at least until up to the level of a floor of the lower part.

38 Claims, 5 Drawing Sheets

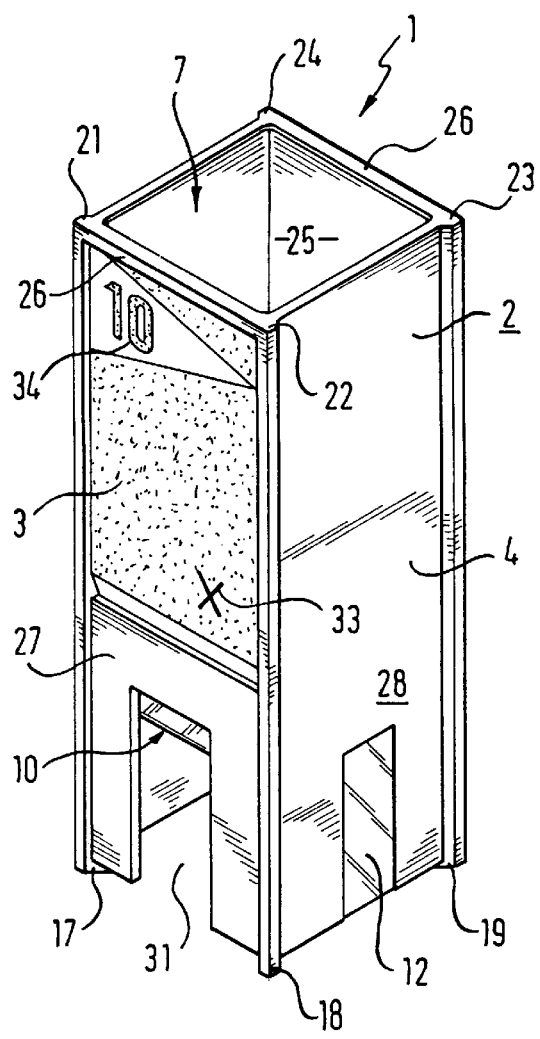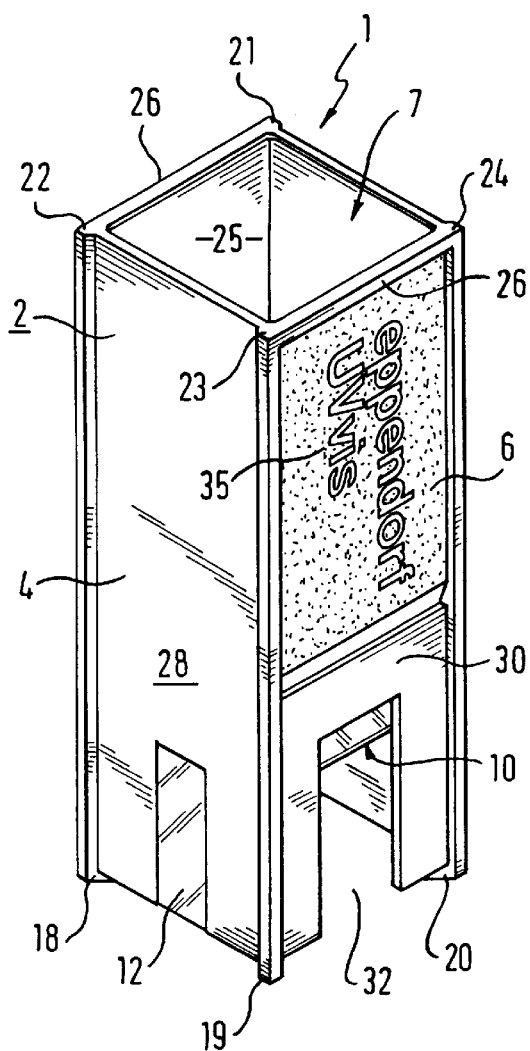

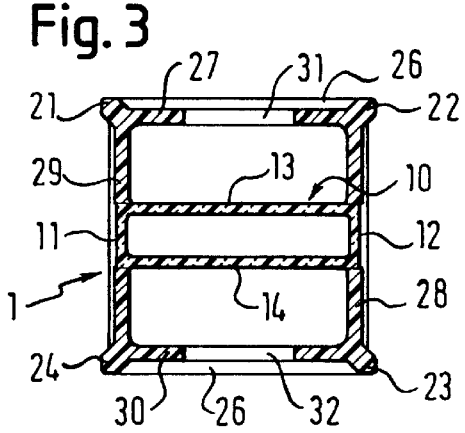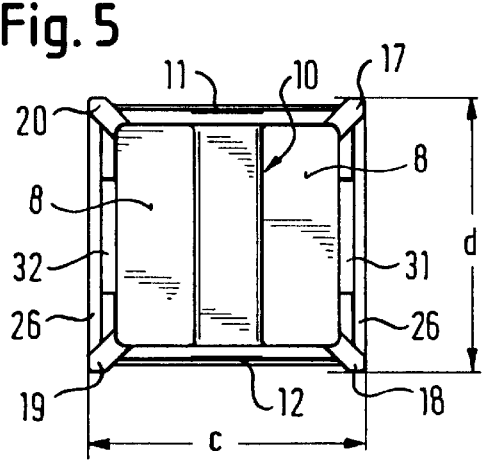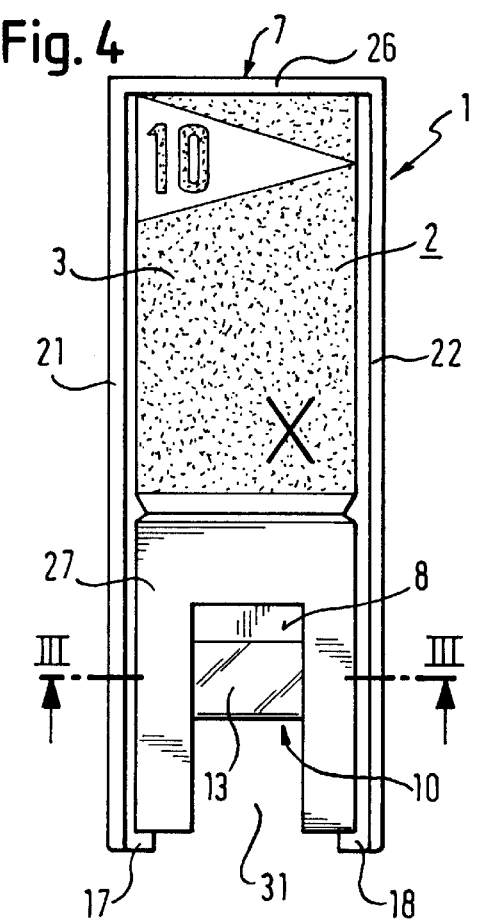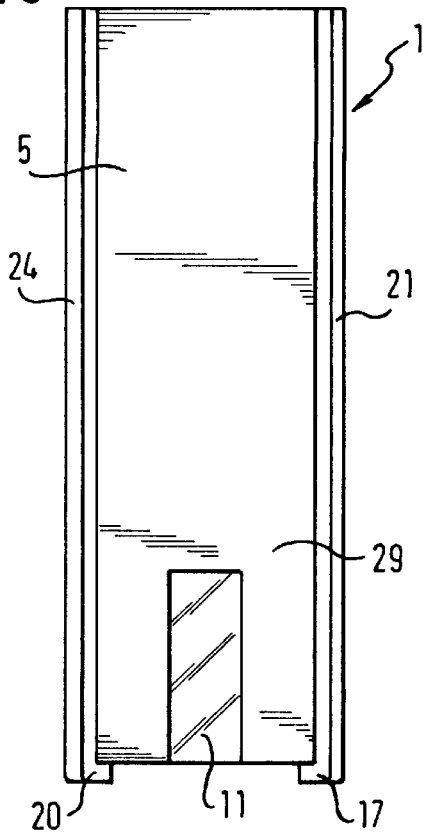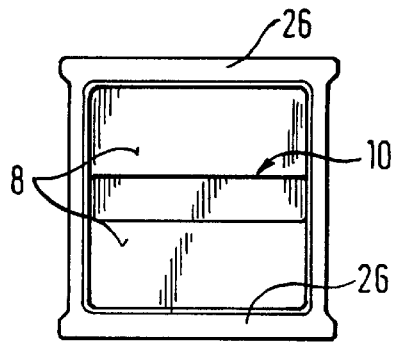

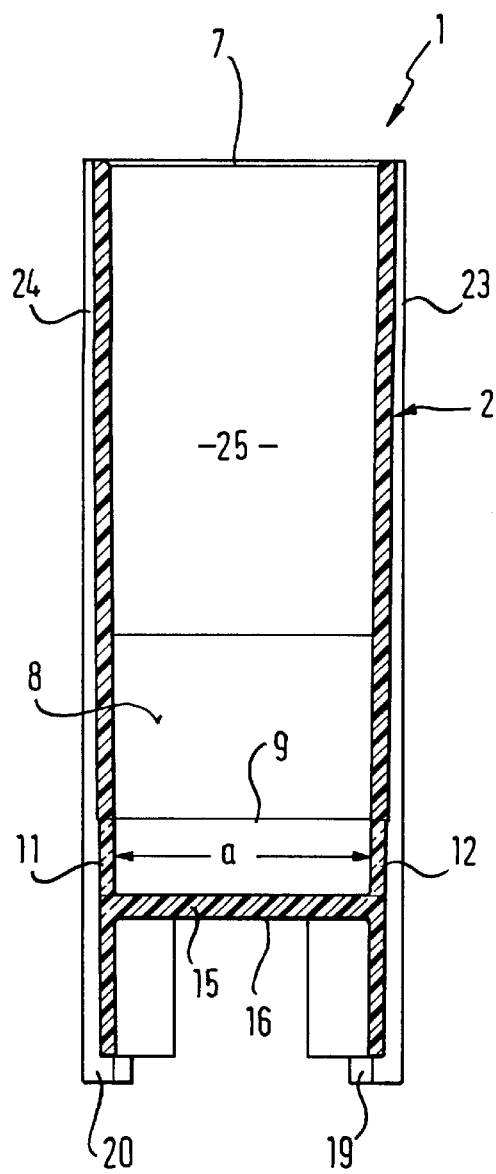
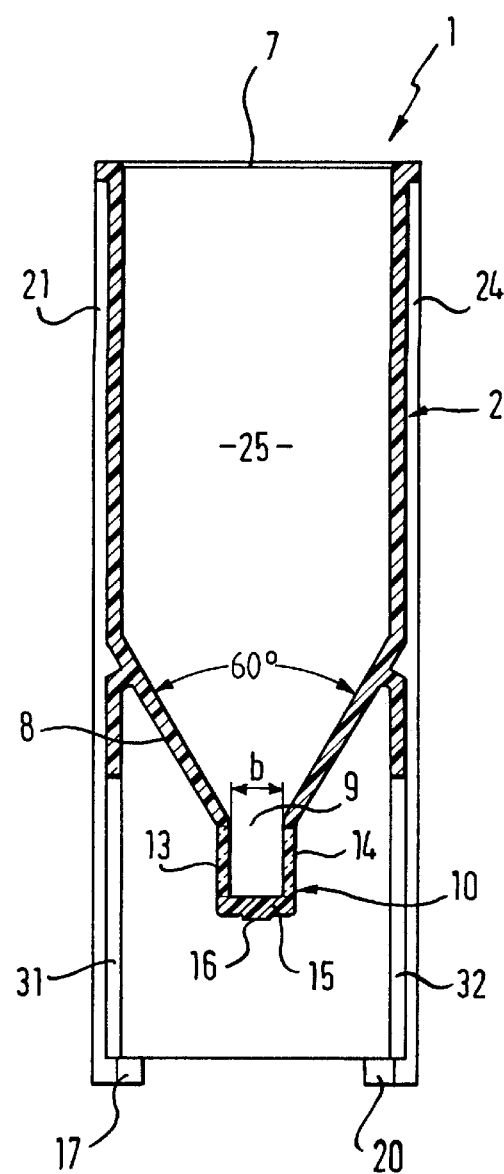

Fig. 13
Fig. 14
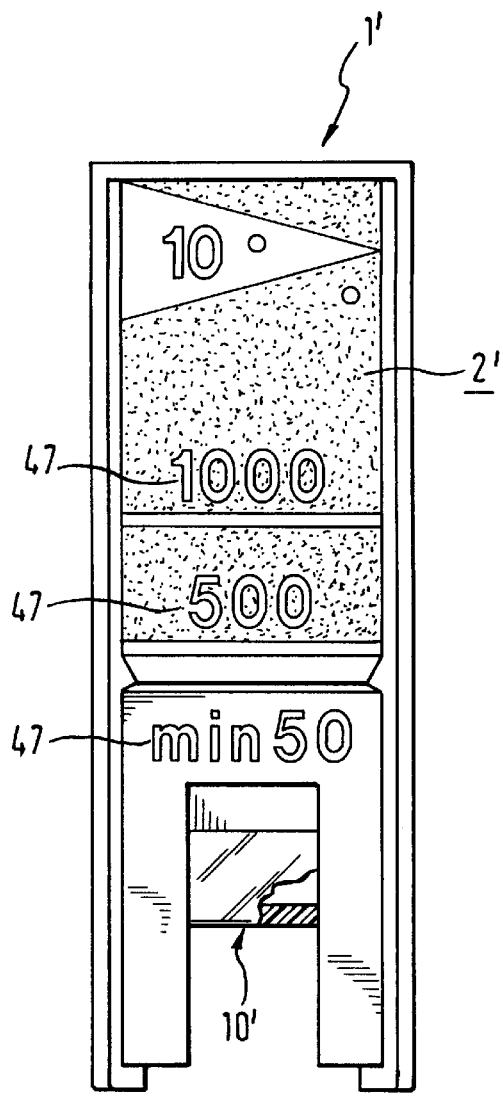
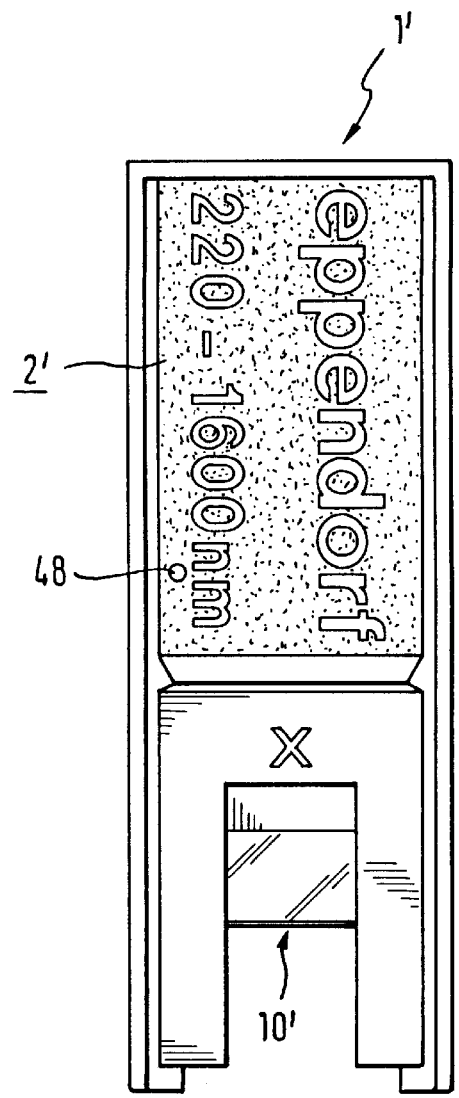

CUVETTE

BACKGROUND OF THE INVENTION

1. Field of the Invention

The invention relates to a cuvette for measuring the absorption of irradiation in liquid samples.

2. Description of the Prior Art

The cuvettes to be taken into account here are used applied in absorption photometers which measure the spectral transmission factor, the spectral retransmission factor or the spectral absorption measure (extinction) of a sample. From the measurement of these values conclusions may be made as to the qualitative or quantitative composition of the sample.

Photometers function in a certain wavelength region, whose selection is effected by color or interference filters. With the spectral photometers on the other hand the light of the illumination means is spectrally disaggregated with a monochromator. With calorimeters the determination of the concentration is effected by color comparison with a standard solution of the same substance. The irradiation may in particular lie in the region of the visible light, in the IR or UV region. The selection may be dependent of the sample to be analyzed. The material selection of the cuvette is in turn directed to the spectral region for which this is to be used.

From DE 17 73 233 C3 there is known a vessel for the optical examination of small fluid quantities which has a lower part with a cross section rectangular on the inside and optically transparent walls and an upper part with larger diagonals than the lower part, wherein the upper part is designed cylindrically. The vessel is closed below and open at the top and at the outside on the lower rectangular part there are attached perpendicular ribs, which extend to the outer dimension of the upper part, wherein the ribs end at a covering on an imagined enveloping cylinder of the upper part. The vessel is suitable as a measuring cuvette and also as a reaction vessel for manual or mechanized sample preparation. The rectangular cross section of the lower vessel part permits two different layer thicknesses for the photometric measurement. The ratio of the layer thicknesses is about 2:1. With this cuvette there is still required a considerable fluid quantity in order to sufficiently fill the lower part for the photometric measurement. Furthermore the stability of the cuvette is not particularly good, since it tapers downwards. Finally there is only a slight variability of the layer thickness.

For the UV region until now cuvettes of quartz glass have been used. These are very expensive and on account of the danger of contamination by the previous sample, on account of the required cleaning work and by way of the danger of breakage they are more unfavorable in the handling.

Indeed for examinations in the UV range often only the smallest of sample quantities are available, without it being known whether these are present in a concentration suitable for a measurement. An example is the DNA photometry with which by measurement in the UV range the ratio of DNA/RNA, the presence of proteins and the opaqueness of a sample are measured. With this it is the case of a routine examination in the genome analysis, for which many times only a small quantity may be branched off. This must be diluted many times in order to fill a cuvette sufficiently with regard to measuring technology. As a result of this the concentration of the sample may be very different. Only after filling into a cuvette may it then be ascertained that with the given concentration and layer thickness a photometric measurement is not possible. Then the sample must be removed, diluted again, again filled into a cuvette and examined. The dilution may however also be so great that the photometric measurement lies on the limit of proof and thus is very erroneous.

Standard cuvettes have a quadratic cross section with outer dimensions of 12.5×12.5 mm. Absorption photometers have a cavity with a corresponding cross section, into which the cuvettes may be inserted. Transversely through this cuvette cavity runs the beam path of the illumination means. Absorption photometers of various manufacturers differ by the distance of the beam path to the floor of the cuvette cavity. Also the irradiation with adsorption photometers of various manufacturers has various cross sections. Until now the cuvette geometries are adapted to the various apparatus types. The use of a single cuvette type for small measuring volumes with various apparatus types is not possible at present.

Furthermore the known plastic cuvettes have a flat bearing in the cuvette cavity. Thus it is difficult to manufacture the cuvettes such they have an exact positioning in the cuvette cavity and do not wobble or jam therein.

Proceeding from this it is the object of the invention to provide a cuvette which favors the adsorption-photometric measurement of the smallest sample quantities of differing concentrations and has an increased stability. Further it is the object of the invention to provide a cuvette which with a simple manufacturability permits a more exact positioning in the cuvette cavity. Finally the object of being able to use a cuvette in absorption photometers with a various arrangement and formation of the beam path is to be achieved.

SUMMARY OF THE INVENTION

According to a first variant of the invention a cuvette for the measurement of the absorption of irradiation in liquid samples which at least in the regions of windows is of a transparent plastic has an inner space, which is formed in an essentially box-shaped upper part with an upper opening for filling and removing sample fluid and in a smaller, essentially box-shaped lower part for the measuring volume, which connects via a transition, preferably a tapering transition, in particular a transition with slants, two pairs of planar parallel windows in the lower part lying opposite one another, wherein the distance of the windows of the one pair is different to the distance of the windows of the other pair, in order to make available various layer thicknesses for the measurement of the samples and four feet flush with the corners of the upper part, which extend away from the upper part at least up to the level of the floor of the lower part.

This cuvette has the measuring chamber in the essentially box-shaped lower part which preferably has a content capacity of maximally 200 µl, preferably about 50 µl. It thus makes do with only very small sample quantities of e.g. minimally about 50 µl. At the same time a funnel-shaped connection between the upper and lower part may simplify the filling and emptying of the cuvettes. On the other hand the sample may also fill up the box-shaped upper part. The whole content capability of the cuvette is formed by the upper and lower part and by way of this has a very large volume region of e.g. about 50 µl to maximally about 2000 µl.

Furthermore by way of the two pairs of windows with a various distance there is a variability of the layer thicknesses for the measurement. Preferably the ratio of the distances is 5:1 so that the variability is very particularly large. For example layer thickness of 10 mm and 2 mm are realized. With this, during the measurement a region switch-over is possible for example in that one rotates the cuvette about 90° into the measuring position without having to pour the sample again or having to reject the sample. For a switch-over of the region by rotating the cuvette, the upper part preferably has a square cross section. Furthermore at the same time as an absorption measurement a fluorescence measurement or luminescence measurement at an angle of 90° to the irradiation axis of the absorption measurement is possible, and specifically on both sides of the cuvette.

Although the cuvette only has a very small measuring chamber and its inner space below is very narrow and small, by way of the four feet extending away from the corners of the upper part at least up to the level of the floor of the lower part, it has a high stability and an exact alignment in the measuring apparatus. The feet may furthermore protect the windows from contact and scratching, in particular when these with respect to the feet are arranged displaced somewhat inwards. The handling of the cuvette and the measuring accuracy are improved by way of this.

For the application in the UV region the cuvette is preferably at least in the region of the windows transparent to UV light. Plastics with a suitable UV transparency are available today. For improving the transparency at least in the region of the windows the wall thickness may be selected very slight (e.g. about 1 mm and below).

In contrast to quartz glass cuvettes such a cuvette may be designed very economically and thus after one usage may be disposed of. Furthermore it has the advantage that is adsorbs much less nucleic acid than glass. This is of particular interest for the further use of the material, since only thus is it possible to almost completely remove the filled volume again. The much more simple closability of a cuvette of plastic favors the reuse of the measuring material. Furthermore by way of the manufacture of the cuvette of plastic, an absence of ribonuclease is ensured, without for this a special working step being necessary.

Furthermore preferably at least the lower part of the cuvette is transparent to visible light. Then one may fill the measuring chamber under observation with a pipette tip. This is particularly advantageous with a very small sample quantity of 50 $\mu$l. Under observation also the mixing of the sample in the small measuring chamber with a pipette tip is more easily possible.

Preferably the cuvette comprises a shielding against foreign light or stray light and/or has a screen. For this it may have an opaque imprint or coloring-in or an opaque inlay part. For this it may however also partly consist of an opaque plastic, i.e. in total of at least two various plastics.

Furthermore between the feet there may be extended walls which are flush with the neighboring limiting walls of the upper part, wherein two oppositely lying walls comprise the parallel windows which have the large distance to one another, and the two further oppositely lying walls comprise openings for beaming through the two further parallel windows which have the smaller distance to one another. The walls may likewise serve as a shielding. Furthermore the further walls protect the windows with the smaller distance from contact and scratching. For this also the windows in the first-mentioned parallel walls may be displaced somewhat inwardly.

Moreover the cuvette in a transparent region may comprise scale markings which permits the user to roughly estimate if he has filled the correct quantity. Also the known filling volume of the lower part may give a hint as to the filled quantity. Inasmuch as this is concerned, scale markings on the upper part may be sufficient, e.g. for 100, 500, and 1000 $\mu$l.

The cuvette may on an outer surface have a field which can be inscripted. This gives the user the possibility of numbering through small series. Furthermore on the cuvette the number of the manufacturing nest may be noted, so that the user may recognize whether he has a cuvette from the same nest and thus there is a very large conformity of the base extinction.

Furthermore the cuvette may carry information within which spectral region measurements may be carried out, e.g. 220 nm to 1200 nm.

Furthermore the cuvette at the upper edge may have at least one grip bulge. This may serve as a hand grip which ensures a secure gripping of the cuvette also with damp fingers. On the other hand it may be used for snapping over the lid which sealingly closes the cuvette. Furthermore the alignment of the cuvette via an edge which is reinforced only in places and/or via an inscription may be recognized in a tactile and/or optical manner.

A filling and/or inner coating of the cuvette with a test tube may be present for the preparation of a chemical reagent.

Preferably the cuvette by way of a mould tool may be manufactured without mould-removal slants, i.e. with a mould removal angle of 0°. This is particularly important for an exact positioning free of play in the cuvette holder or the cuvette cavity and for the error-free optical imaging by way of the function of a planar-parallel plate and not that of a prism which is formed by the mould removal slants. The prism would cause a light beam deflection.

According to a second variant of the invention a cuvette for the measurement of the adsorption of beams in liquid probes has a cuvette body in which there is formed an inner space for receiving sample fluid and which comprises at least one pair of planar-parallel windows lying opposite one another at a distance, which on four corners comprises protruding ribs running axially at least over a part of the height of the cuvette body, wherein the whole cuvette cross section is arranged within imagined connecting lines through the end points of the ribs. By way of this it is possible to support the cuvette only on the end points of the ribs in the cuvette cavity. Since the ribs may be manufactured with an excellent parallelity, by way of this a very exact positioning of the cuvette in the cuvette cavity is achieved. Furthermore the ribs favor the use of the cuvette in a different apparatus with the use of an adapter which in the following is described in more detail. The cuvette of the second variant of the invention may be equipped with one or more features of the first variant of the invention.

According to a third variant of the invention a cuvette may be applied into an adapter which comprises light passage openings allocated to the measuring windows of the cuvette and a standing surface which is arranged on the same level or below a standing surface of a cuvette. The distance of the standing surface to the light passage openings of the adapter is matched to the arrangement and formation of the beam path in the cuvette cavity of the apparatus to be applied. Also when the cuvette is to be applied in the apparatus for which it is designed, an adapter may be used whose standing surfaces are arranged on the same level as the standing surface of the cuvette. For this the floor of the adapter may comprise recesses at the corners which accommodate feet of the cuvette. Furthermore the cuvette may have a coaster whose height determines the distance of its standing surface to the light passage openings. The coaster may be exchangeable in order to use the adapter for various apparatus. Thus the windows of the cuvette may always be arranged correctly in the beam path by application of the adapter. At the same time the adapter may serve as a shielding against foreign light or stray light and/or serve as a screen which screens out part of the beam. The adapter also protects the cuvette from contact and scratching. According to a special formation of the cuvette it may be applied in various rotational positions in order to permit various layer thicknesses. Furthermore the adapter may comprise a grip tap protruding upwards which permits a simple insertion and removal in the cuvette cavity, and may be a surface for inscription.

Preferably the adapter is box-shaped with lateral walls towering from a floor, which at the corners end at a distance to one another and in the distancing region accommodate the ribs of the cuvettes. By way of this it is possible for the adapter not to protrude beyond the outer dimensions of the cuvette defined by the end points of the ribs, but rather to disappear in the contour of the cuvette. The adapter thus does not impose on the cuvette volume and together with the cuvette may be applied into any cuvette cavity with a standardized cross section. Thus the cuvette with and without adapter can be applied in various rotational positions into the cuvette cavity.

The cuvette of the third variant of the invention may be a cuvette known from the state of the art, it is however preferably equipped with one or more features of the first and/or second variant of the invention.

BRIEF DESCRIPTION OF THE DRAWINGS

The invention is hereinafter described in more detail by way of the accompanying drawings. In the drawings there are shown:

FIG. 1 a cuvette in a perspective view of the front and right side obliquely from above;

FIG. 2 the cuvette in a perspective view of the right and rearside obliquely from above;

FIG. 3 the cuvette sectioned along the line III—III of FIG. 4;

FIG. 4 the cuvette in a front view;

FIG. 5 the cuvette in a view from below;

FIG. 6 the cuvette in a view from the left side;

FIG. 7 the cuvette in a plan view;

FIG. 8 the cuvette in a vertical section parallel to the front side;

FIG. 9 the cuvette in a vertical section perpendicular to the front side;

FIG. 13 another cuvette in a front view;

FIG. 14 the cuvette in a rear view.

DETAILED DESCRIPTION OF THE PREFERRED EMBODIMENTS

Figure 10:
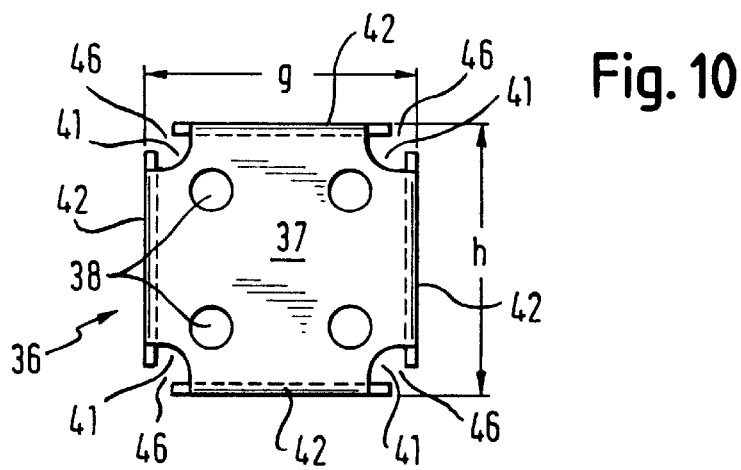
FIG. 10 an adapter in a view from below.

The cuvette 1 shown in the FIGS. 1 to 9 has an essentially box-shaped upper part 2 with a front limiting wall 3, two lateral limiting walls 4, 5 and a rear limiting wall 6. Furthermore the upper part 2 comprises an upper, axially aligned opening 7 and a transition 8 which in a vertical section perpendicular to the front and rear limiting walls 3, 6 is funnel-shaped. The opening angle of the funnel-shaped transition 8 is for example 60°.

The transition 8 has a lower opening 9 to an essentially box-shaped lower part 10. The lateral limiting walls thereof are formed by two pairs of planar-parallel windows 11, 12 and 13, 14, wherein the distance between the innersides a of the first-mentioned windows 11, 12 is distinctly larger than the distance between the inner side b of the second-mentioned windows 13, 14 (cf. FIGS. 8, 9). As an example the distance a is selected at 10 mm and the distance b at 2 mm. Below the lower part is closed by an essentially planar floor 15 at which centrally the injection location 16 is located.

From the four corners of the upper part 2 there extend axially four feet 17 to 20 up to a level distinctly below the floor 15. From the four corners of the cuvette 1 there outwardly project ribs 21 to 24 which extend over the whole length of the upper part 2 and of the feet 17 to 20 and in cross section are arrow-shaped (cf- FIGS. 3, 5). The end points of the ribs 21 to 24 tenter a square with the edge lengths c, d which corresponds to the inner cross section of the cuvette cavity. This has standard dimensions of 12.5×12.5 mm.

The inner space 25 formed in the upper part 2 and lower part 10 has in the example a total volume of 2000 μl, wherein the volume of the lower part is only 50 μl.

The cuvette 1 has at the upper edge in the region of the front limiting wall 3 and of the rear limiting wall 6 outwardly protruding gripping bulges 26 which are flush with the "arrow tips" of the ribs 21, 24 or 22, 23.

The distancing region between the feet 17 to 20 is bridged by walls 27 to 30 which are extensions of the walls 3 to 6. The walls 27 to 30 end somewhat above the feet 17 to 20, but significantly below the floor 15.

The walls 27 and 30 have in each case a rectangular opening 31, 32 extending up to their lower end, these permitting a light passage through the windows 13, 14 of the lower part 10, which are located at a distance to the walls 27, 30.

The walls 28, 29 are at the same time limitings walls of the lower part 10 in which the windows 11, 12 are formed displaced somewhat inwards. For reasons of manufacturing technology the inwardly displaced regions of the walls 28, 29 likewise extend up to The cuvette 1 is as a whole injection moulded from a UV-transparent plastic, and specifically in a mould tool which does not comprise mould removal slants at the important surfaces. On the front limiting wall 3 the cuvettes 1 at 33 carry a recognition which indicates the nest of the injection molding tool from which the respective cuvette 1 originates. Furthermore on the walls 3, 6 there are located inscriptions 34, 35 which relate to the alignment of the cuvettes, there origin and their purpose. Furthermore the surfaces of these limiting walls 3, 6 are roughened in order to permit a tactile acquisition of the orientation. For this there may serve edge bulges 26, likewise serving the secure gripping.

The cuvette 1 on account of its four standing feet 17, 20 has a secure standing also outside an adsorption photometer. The ribs 21 to 24 ensure a secure positioning in the cuvette cavity without the risk of jamming. The cuvette 1 on account of its shaping and form can be easily filled also with small sample quantities, since a pipette tip under observation can be led through the upper opening 7 until into the lower part 10. On account of the low content capability of the latter, sample quantities of 50 μl are sufficient.

The cuvette may be brought into two various orientations into the beam path, e.g. for a measurement with a different thickness.

Figure 11:
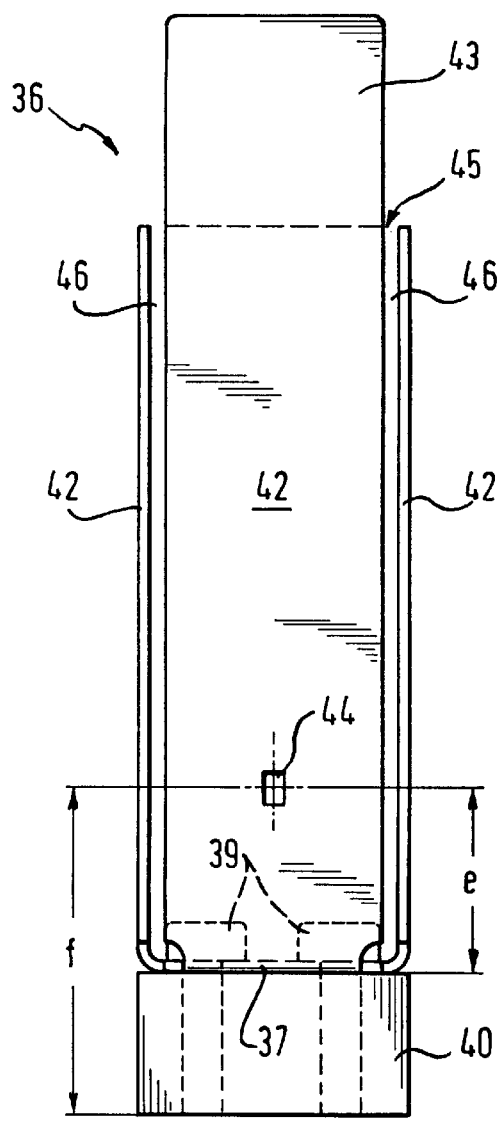
FIG. 11 the adapter in a front view.
Figure 12:
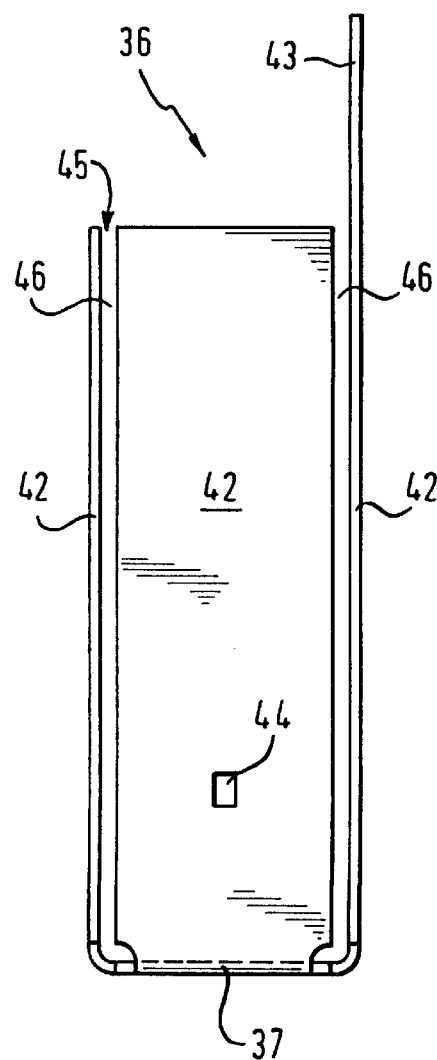
FIG. 12 the adapter in a view from the right side.

The previously described cuvette 1 can be applied into an absorption photometer in which the distance of the beam path to the floor of the cuvette cavity corresponds to the distance of the standing surfaces of the feet 17, 20 to the through-irradiation plane of the windows (corresponds to section plane III—III in FIG. 4). The cuvette can however also be applied into other apparatus if the adapter 36 according to FIGS. 10 to 12 is used.

The adapter 36 has a floor 37 with four holes 38. Through these there may be guided screws 39 in order to fix a coaster 40 on the lower side of the floor 37. In the corners the floor has quarter-circle shaped recesses 41.

From the sides of the floor 37 there towers lateral walls 42 of which one at the top is extended by a gripping tab 43. In all lateral walls 42 there are formed approximate rectangular light passage openings 44. The distance e of the centre of the light passage openings 44 to the lower side of the floor 37 matches with the distance of the standing surfaces of the feet 17 to 20 to the through-irradiation plane of the lower part 10. The distance f corresponds to the distance of the beam path to the cavity floor.

The lateral walls 42 border a recess 45 for a cuvette 1. At the four corners of the receiver 45 they end at a distance to one another, wherein the distance regions 46 may accommodate the ribs 21 to 24. The walls 27 to 30 of an inserted cuvette are supported just on the upper side of the floor 37 of the adapter and the feet 17 to 20 project just up to the lower side of the floor 37.

The outer dimensions g and h of the adapter 36 correspond to the dimensions c and d of the cuvette 1. The adapter 36 and an inserted cuvette 1 thus form one unit, which fits exactly into a cuvette cavity.

The adapter 36 without a coaster 40 with an inserted cuvette may be inserted into the cuvette cavity of an apparatus for which the cuvette is designed. The adapter 36 then serves as a handle, shielding and screen for the cuvette.

With a coaster 40 the adapter 36 permits the use of the cuvette 1 in another type of apparatus. Then the cuvette likewise serves as a handle, shielding and screen. An adaptation to another apparatus is possible by exchanging the coaster 40.

The tab 43 is so long that with all apparatus to be considered it protrudes out of the cuvette cavity and may be easily gripped. It may also be used for inscription purposes.

The FIGS. 13 and 14 show a cuvette 1', which differs from the cuvette 1 of the FIGS. 1 to 9 by additional filling condition details 47, which are allocated to the upper part 2' and the lower part 10'. Furthermore it carries information 48 as to the spectral region useful for the measurements.

What is claimed is:

1. A cuvette for measuring absorption of irradiation in liquid probes, comprising:
    a substantially rectangular body having an inner space for receiving a sample liquid probe and at least one pair of planar parallel windows spaced from each other and extending parallel to each other; and
    four ribs provided on four corners of the body, respectively, and extending at least over a portion of a body height, an entire cross-section of the cuvette lying within imaginary limiting lines connecting end points of the four rib,
    wherein the inner space is formed in an essentially box-shaped upper part with an upper opening for filling and removing sample fluid, and in a smaller, essentially box-shaped lower part for the measuring volume connected with the upper part via a transition, wherein the cuvette has two pairs of planar-parallel windows provided in the lower part which lie opposite one another, wherein a distance of the windows of one pair is different from a distance of the windows of another pair in order to make available various layer thickness of the sample fluid for measurement of samples, and four feet flush with the corners of the upper part which extend away from the upper part at least up to the level of the floor of the lower part.

2. A cuvette according to claim 1, wherein the inner space is formed in an essentially box-shaped upper part with an upper opening for filling and removing sample fluid, and in a smaller, essentially box-shaped lower part for the measuring volume connected with the upper part via a transition, wherein the cuvette has two pairs of planar-parallel windows provided in the lower part which lie opposite one another, wherein a distance of the windows of one pair is different from a distance of the windows of another pair in order to make available various layer thickness of the sample fluid for measurement of samples, and four feet flush with the corners of the upper part which extend away from the upper part at least up to the level of the floor of the lower part.

3. A cuvette according to claim 1 wherein the total content capacity of the inner space is at least 1000 $\mu$l.

4. A cuvette according to claim 1 wherein the total content capacity of the inner space is about 2000 $\mu$l.

5. A cuvette according to claim 1 wherein the upper part has an essentially square cross-section.

6. A cuvette according to claim 1 wherein content capacity of the lower part is about 50 $\mu$l.

7. A cuvette according to claim 1, wherein ration of the distances between the parallel windows of the two parts is 5:1.

8. A cuvette according to claim 1, wherein the distance between the windows of one of the two pairs of planar-parallel windows is 10 mm.

9. A cuvette according to claim 1, wherein the distance between the windows of another of the two pairs of planar-parallel windows is 2 mm.

10. A cuvette according to claim 1, wherein the cuvette, at least in a region of the windows, is UV-transparent.

11. A cuvette according to claim 1, wherein at least the lower part is transparent to visible light.

12. A cuvette according to claim 1, wherein the upper part has a funnel-shaped floor.

13. A cuvette according to claim 1, further comprising at least one shielding against at least one of foreign light, and stray light and a screen.

14. A cuvette according to claim 13, wherein the at least one of shielding and screen comprises an opaque inscription or coloring in.

15. A cuvette according to claim 13, comprising a opaque inlay part forming the at least one of shielding and screen.

16. A cuvette according to claim 13, wherein the cuvette partly consists of a opaque plastic forming the at least one of shielding and screen.

17. A cuvette according to claim 1, wherein the body has, between the feet, extended walls which are flush with neighboring limiting walls of the upper part, wherein two oppositely lying walls comprise the windows which have the larger distance therebetween, and two, further oppositely lying walls comprise openings for beaming through the two windows which have the smaller distance therebetween.

18. A cuvette according to claim 17, wherein the extended walls compromise inwardly displaced windows.

19. A cuvette according to claim 17, wherein the walls extend from the upper part at least up to the level of the floor of the lower part.

20. A cuvette according to claim 1, wherein the feet are extended away from the upper part at least up to the lower edge of the walls arranged between them.

21. A cuvette according to claim 1, further comprising scale markings.

22. A cuvette according to claim 1, comprising a field which can be inscribed.

23. A cuvette according to claim 1, comprising an indication with a number of a manufacturing nest.

24. A cuvette according to claim 1, having at the upper edge, at least one gripping bulge.

25. A cuvette according to claim 24, comprising a lid snapped over the gripping bulge.

26. A cuvette according to claim 1, comprising a hinged lid.

27. A cuvette according to claim 1, comprising at least one of filling and inner coating with a reactant.

28. A cuvette according to claim 1 wherein the ribs are essentially extended over the entire length of the upper part and of the feet.

29. A cuvette assembly comprising:

A rectangular body having an inner space for receiving a sample liquid probe and at least one pair of planar parallel windows spaced from each other and extending parallel to each other;

four ribs provided on four corners of the body, respectively, and extending at least over a portion of a body height, an entire cross-section of the cuvette lying within imaginary limiting lines connecting end points of the four ribs, and a standing surface; and an adapter for receiving the cuvette and having light passage openings corresponding to locations of the cuvette windows, and a standing surface which is located in one of a plane the cuvette standing surface is located in, and a plane located below the cuvette standing plane, wherein the adapter is box-shaped and has lateral wall extending upward from an adapter floor, and a cross-section of the box-shaped adapter is so selected that corners thereof accommodate the cuvette ribs.

30. A cuvette assembly according to claim 29 wherein the adapter is box-shaped and has lateral wall extending upward from an adapter floor, and a cross-section of the box-shaped adapter is so selected that corners thereof accommodate the cuvette ribs.

31. A cuvette according to claim 29, wherein the adapter has a lateral dimension not extending beyond a maximum outer dimensions of the cuvette.

32. A cuvette according to claim 29, wherein the adapter has a floor which at the corner, comprises recesses which accommodate feet of the cuvette.

33. A cuvette according to claim 29, wherein the adapter comprises an upwardly projecting gripping tab.

34. A cuvette according to claim 29, wherein the adapter comprises a surface for writing.

35. A cuvette according to claim 29, wherein the adapter comprises a coaster.

36. A cuvette according to claim 35, wherein the adapter comprises means for releasably connecting the coaster to an adapter floor.

37. A cuvette assembly according to claim 35, wherein the adapter comprises means for snapping the coaster into the floor.

38. A cuvette assembly according to claim 29, comprising a foil packaging wrapped around the assembly, which is free from desoyxribounclease and ribonuclease.

* * * * *